(12) United States Patent
Blus et al.

(10) Patent No.: US 11,135,032 B2
(45) Date of Patent: Oct. 5, 2021

(54) ELECTROSURGICAL ILLUMINATING INSTRUMENT

(71) Applicant: GYRUS ACMI, INC., Southborough, MA (US)

(72) Inventors: Theodore C. Blus, Shoreview, MN (US); Jyue Boon Lim, New Brighton, MN (US); Kester J. Batchelor, Mound, MN (US)

(73) Assignee: Gyrus Acmi, Inc., Westborough, MA (US)

( * ) Notice: Subject to any disclaimer, the term of this patent is extended or adjusted under 35 U.S.C. 154(b) by 111 days.

(21) Appl. No.: 16/090,954

(22) PCT Filed: Apr. 4, 2016

(86) PCT No.: PCT/US2016/025849
§ 371 (c)(1),
(2) Date: Oct. 3, 2018

(87) PCT Pub. No.: WO2017/176240
PCT Pub. Date: Oct. 12, 2017

(65) Prior Publication Data
US 2019/0133710 A1 May 9, 2019

(51) Int. Cl.
*A61B 18/14* (2006.01)
*A61B 90/30* (2016.01)
(Continued)

(52) U.S. Cl.
CPC ............ *A61B 90/30* (2016.02); *A61B 18/14* (2013.01); *A61B 18/1402* (2013.01); *A61B 90/08* (2016.02); *A61B 2018/00589* (2013.01); *A61B 2018/00595* (2013.01); *A61B 2090/0807* (2016.02); *A61B 2090/306* (2016.02); *A61B 2090/308* (2016.02)

(58) Field of Classification Search
CPC .............. A61B 90/30; A61B 2090/306; A61B 18/1402
USPC ................................................ 600/247–249
See application file for complete search history.

(56) References Cited

U.S. PATENT DOCUMENTS 2,246,836 A 6/1941 Campbell
3,858,586 A 1/1975 Lessen
(Continued)

FOREIGN PATENT DOCUMENTS

EP 1330991 B1 9/2007
EP 2027824 A1 2/2009
(Continued)

OTHER PUBLICATIONS

SABIC, "Ultem.TM Resin", https://www.sabic.com/en/products/specialties/ultem-resins/ultem-resin, accessed May 19, 2020. (Year: 2020).*

(Continued)

*Primary Examiner* — Amy R Sipp
(74) *Attorney, Agent, or Firm* — Schwegman Lundberg & Woessner, P.A.

(57) ABSTRACT

An electrosurgical instrument includes a light source, a first conductor, a second conductor, an insulation material positioned between the first conductor and the second conductor, and a light pipe that carries light from the light source to the insulation material.

14 Claims, 2 Drawing Sheets

(51) Int. Cl.
*A61B 18/00* (2006.01)
*A61B 90/00* (2016.01)

(56) References Cited

U.S. PATENT DOCUMENTS

| | | | |
|---|---|---|---|
| 4,467,812 A | | 8/1984 | Stoller |
| 4,562,832 A | | 1/1986 | Wilder et al. |
| 4,597,030 A | | 6/1986 | Brody et al. |
| 4,597,383 A | | 7/1986 | Vanderbel |
| 4,688,569 A | | 8/1987 | Rabinowitz |
| 4,800,878 A | | 1/1989 | Cartmell |
| 4,839,492 A | | 6/1989 | Bouchier et al. |
| 5,203,353 A | | 4/1993 | Easley et al. |
| 5,376,087 A | | 12/1994 | Haber et al. |
| 5,394,863 A | | 3/1995 | Sanford et al. |
| 5,401,272 A | | 3/1995 | Perkins |
| 5,445,142 A | * | 8/1995 | Hassler, Jr. ........ A61B 1/00087 600/105 |
| 5,449,356 A | | 9/1995 | Walbrink et al. |
| 5,626,578 A | | 5/1997 | Tihon |
| 5,674,184 A | | 10/1997 | Hassler, Jr. |
| 5,683,350 A | * | 11/1997 | Paul ................. A61B 1/24 362/186 |
| 5,754,719 A | | 5/1998 | Chen et al. |
| 5,762,613 A | | 6/1998 | Sutton et al. |
| 5,817,091 A | | 10/1998 | Nardella et al. |
| 6,193,714 B1 | | 2/2001 | McGaffigan et al. |
| 6,213,618 B1 | | 4/2001 | Dobbin et al. |
| 6,290,368 B1 | | 9/2001 | Lehrer |
| 6,428,180 B1 | | 8/2002 | Karram et al. |
| 6,516,216 B1 | | 2/2003 | Fontenot et al. |
| 6,585,727 B1 | | 7/2003 | Cashman et al. |
| 6,676,660 B2 | | 1/2004 | Wampler et al. |
| 7,083,620 B2 | | 8/2006 | Jahns et al. |
| 7,871,375 B2 | | 1/2011 | Talieh |
| 8,025,661 B2 | | 9/2011 | Arnold et al. |
| 8,287,534 B2 | | 10/2012 | Balog |
| 8,419,729 B2 | | 4/2013 | Ibrahim et al. |
| 8,506,565 B2 | | 8/2013 | DeCarlo |
| 2002/0038121 A1 | | 3/2002 | Rozenberg |
| 2004/0167513 A1 | | 8/2004 | Hilal |
| 2006/0069386 A1 | | 3/2006 | Dubnack et al. |
| 2006/0271042 A1 | | 11/2006 | Latterell et al. |
| 2006/0293645 A1 | | 12/2006 | Hibner |
| 2007/0049927 A1 | | 3/2007 | Saltzman |
| 2008/0086117 A1 | | 4/2008 | Cao |
| 2008/0312649 A1 | | 12/2008 | Guerra et al. |
| 2009/0054890 A1 | * | 2/2009 | DeCarlo ............. A61B 90/36 606/34 |
| 2009/0076334 A1 | | 3/2009 | Chen |
| 2010/0125172 A1 | | 5/2010 | Jayaraj |
| 2010/0145333 A1 | * | 6/2010 | Dethier ............. A61B 18/1402 606/42 |
| 2010/0198200 A1 | | 8/2010 | Horvath |
| 2010/0268221 A1 | | 10/2010 | Beller et al. |
| 2010/0312241 A1 | | 12/2010 | Erickson, Jr. |
| 2011/0060332 A1 | * | 3/2011 | Cheng ................. A61B 1/0684 606/42 |
| 2012/0116267 A1 | | 5/2012 | Kimball et al. |
| 2012/0330324 A1 | | 12/2012 | Sauer |
| 2013/0197317 A1 | * | 8/2013 | Daniel ................. A61B 1/0684 600/249 |
| 2013/0267787 A1 | | 10/2013 | Warnock |
| 2014/0218962 A1 | | 8/2014 | Waters |
| 2016/0045247 A1 | | 2/2016 | Heim et al. |

FOREIGN PATENT DOCUMENTS

| | | |
|---|---|---|
| WO | WO-2008014465 A2 | 1/2008 |
| WO | WO-2009005850 A1 | 1/2009 |
| WO | WO-2017176240 A1 | 10/2017 |

OTHER PUBLICATIONS

"International Application Serial No. PCT/US2016/025849, International Preliminary Report on Patentability dated Oct. 18, 2018", 7 pgs.

"International Application Serial No. PCT/US2016/025849, International Search Report dated Dec. 21, 2016", 4 pgs.

"International Application Serial No. PCT/US2016/025849, Written Opinion dated Dec. 21, 2016", 5 pgs.

* cited by examiner

ELECTROSURGICAL ILLUMINATING INSTRUMENT

RELATED APPLICATION

This application is a U.S. National application filed under 35 U.S.C. 371 claiming priority to International Application No. PCT/US2016025849, filed on Apr. 4, 2016.

FIELD

The present disclosure relates to an electrosurgical instrument. More specifically, the present disclosure relates to an electrosurgical illuminating instrument.

BACKGROUND

The statements in this section merely provide background information related to the present disclosure and may or may not constitute prior art.

Electrosurgical illuminating instruments have become widely employed by medical professionals in recent years. A number of electrosurgical illuminating instruments have been developed whereby an active electrode is attached to an insulated handle and a high frequency current is applied thereto. Accordingly, electrosurgical illuminating instruments are used by medical professionals in various types of surgical procedures. A common surgical procedure involves cauterizing a patient's tissue. Typically, cauterizing is employed to sterilize and cut tissue as well as to kill certain tissue that has been infected with disease such as cancer and the like. To accurately perform the surgical procedure, the medical professional needs to be able to illuminate and view the local tissue area to be cauterized. Thus, it is imperative that adequate lighting be provided to the affected regions during the surgical procedure. Overhead surgery room lighting, however, is rarely sufficient. Accordingly, various types of supplemental lighting equipment have been developed that suits different medical illumination requirements, for example, the incorporation of a lighting source to a surgical instrument.

Most existing surgical light sources involve fiber optic cable or bundles that are permanently attached to a particular surgical instrument with one end of the fiber optic cable or bundle connected to a source of illumination. These types of surgical instrument lights are disclosed in U.S. Pat. Nos. 6,585,727; 5,376,087; and 4,688,569. Such instruments, however, are cumbersome to manufacture and to use in a surgery room setting.

Accordingly, there is need for a surgical instrument that incorporates an effective light source.

SUMMARY

The present invention provides an electrosurgical illuminating instrument.

Accordingly, pursuant to one aspect of the present invention, an electrosurgical instrument includes a light source, a first conductor, a second conductor, an insulation material positioned between the first conductor and the second conductor, and a light pipe that carries light from the light source to the insulation material.

Accordingly, pursuant to another aspect of the present invention, an electrosurgical instrument includes a light source, a first conductor, a second conductor, and an insulation material positioned between the first conductor and the second conductor, the insulation material being a light pipe that carries light from the light source.

The above aspects of the present invention can be further characterized by one or any combination of the features described herein, such as: the insulation material is translucent, transparent or both translucent and transparent; a portion of the insulation material is opaque; a handpiece, the light source being positioned in the handpiece; an extension with a proximal end and a distal end, the proximal end of the extension being connected to the handpiece, the first conductor and the second conductor being positioned at the distal end of the extension; the first conductor, the second conductor and the insulation material are configured to illuminate a surgical site; the insulation material has an exterior surface that transmits the incident light; the surface that transmits the incident light is located at the distal ends of the first and second conductors, the lateral sides of the first and second conductors, or both the distal ends and the lateral sides of the first and second conductors; the first conductor, the second conductor and the insulation material are configured to display an instrument state of the electrosurgical instrument; the electrosurgical instrument is capable of delivering a therapy current between the first conductor and the second conductor; the insulation material has a frosted surface to diffuse the light; at least of a portion of the insulation material is an indicator that displays an instrument state of the electrosurgical instrument; the insulation material is made from a material selected from a group consisting of ceramic, silicon rubber, glass, and titanium dioxide; the light source is an LED; and the first conductor is a first electrode and the second conductor is a second electrode.

Accordingly, pursuant to another aspect of the present invention, an electrosurgical instrument includes a handpiece, a surgical end, a light source positioned in the handpiece, and a light pipe with a proximal end and distal end. The proximal end of the light pipe selectively engages optically with the light source to transmit light to the distal end of the light pipe such that light is transmitted to the surgical end which converts from wide illumination to tip illumination of a surgical site.

This aspect of the present invention can be further characterized by one or any combination of the features described herein, such as: the surgical end includes a first electrode, a second electrode, and an insulation layer positioned between the first electrode and the second electrode; the light pipe transmits light from the light source to the insulation layer; the insulation material is translucent, transparent or both translucent and transparent; a portion of the insulation material is opaque; the first conductor, the second conductor, and the insulation material are configured to display an instrument state of the electrosurgical instrument; the insulation material has a frosted surface to diffuse the light; the insulation material is made from a material selected from a group consisting of ceramic, silicon rubber, glass, and titanium dioxide; the light source is an LED.

Accordingly, pursuant to yet another aspect of the present invention, an electrosurgical instrument includes a handpiece, a light source positioned in the handpiece, a surgical end with a first electrode, a second electrode, and an insulation material positioned between the first electrode and the second electrode; and a light pipe that carries light from the light source to the insulation material.

This aspect of the present invention can be further characterized by one or any combination of the features described herein, such as: the light pipe has a proximal end and distal end, the proximal end of the light pipe selectively engaging optically with the light source to transmit light to the distal end of the light pipe such that light is transmitted to the surgical end which converts from wide illumination to tip illumination of a surgical site; the insulation material is translucent, transparent or both translucent and transparent; a portion of the insulation material is opaque; an extension with a proximal end and a distal end, the proximal end of the extension being connected to the handpiece, the first electrode and the second electrode being positioned at the distal end of the extension; the first electrode, the second electrode and the insulation material are configured to illuminate a surgical site; the first electrode, the second electrode and the insulation material are configured to display an instrument state of the electrosurgical instrument; the insulation material has a frosted surface to diffuse the light; the insulation material is made from a material selected from a group consisting of ceramic, silicon rubber, glass, and titanium dioxide; and the light source is an LED.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely exemplary in nature and is not intended to limit the present disclosure, application, or uses.

Figure 1:
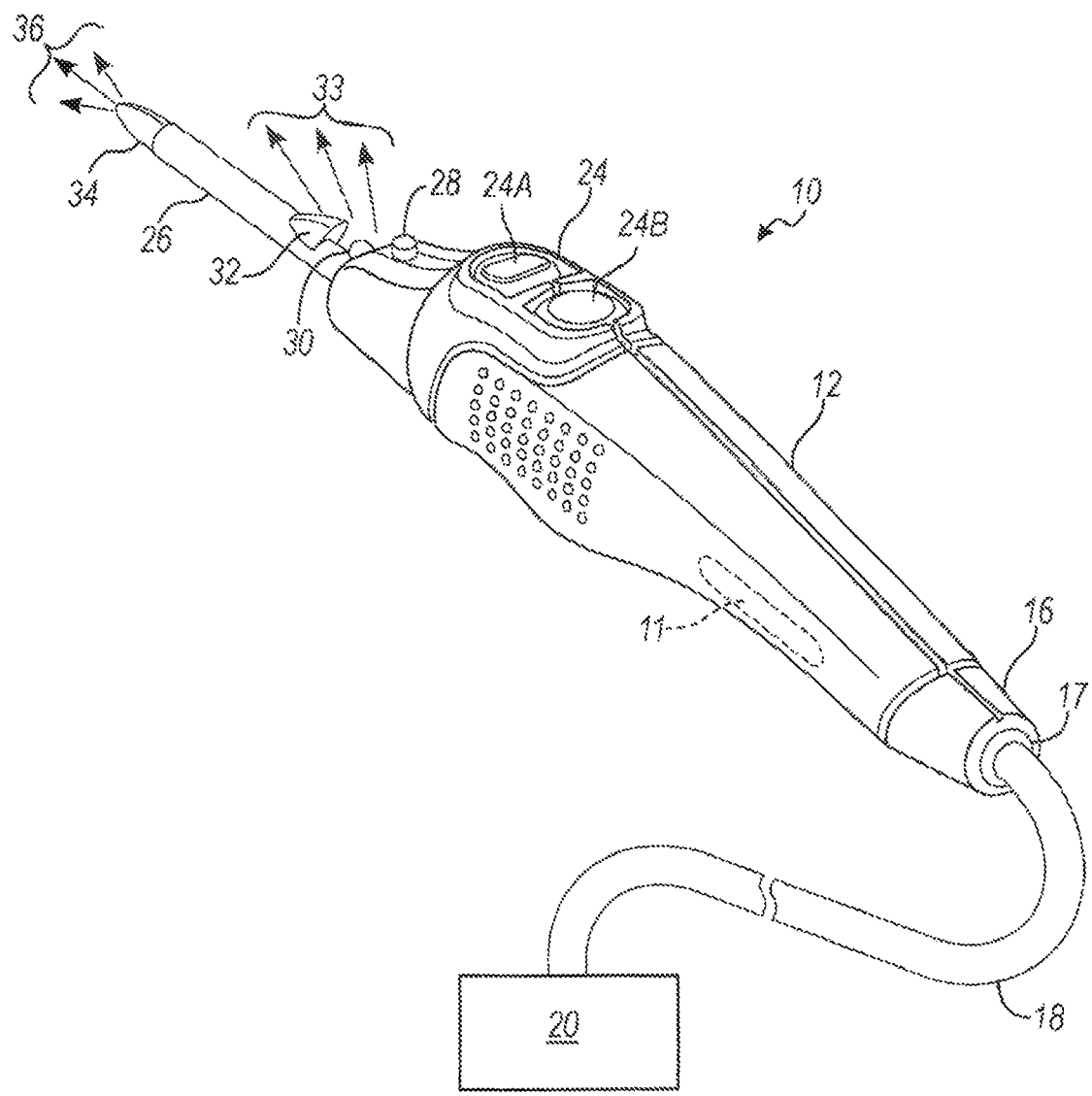
FIG. 1 is a perspective view of an electrosurgical illuminating instrument in accordance with the principles of the present invention.
Figure 2:
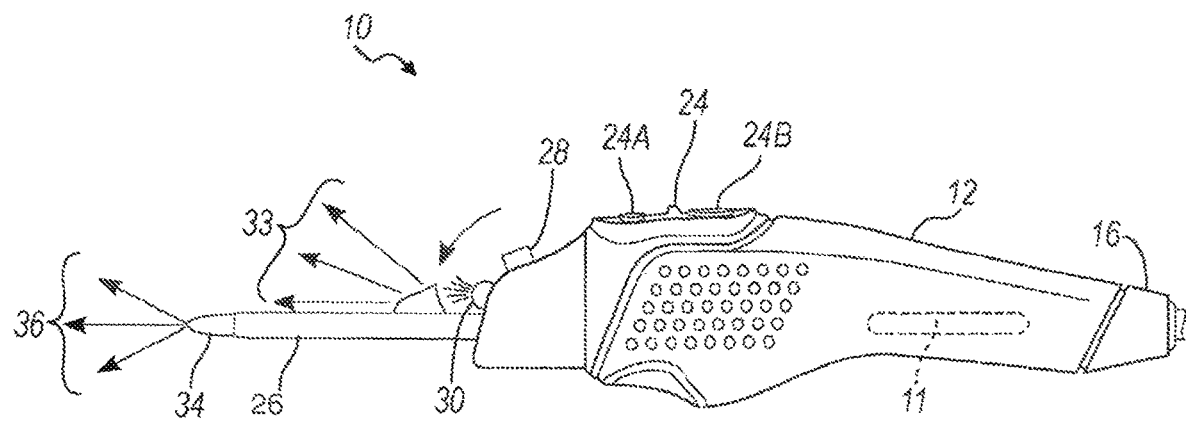
FIG. 2 is a side view of the electrosurgical illuminating instrument.

With reference to FIG. 1, an electrosurgical illuminating instrument embodying the principles of the present invention is illustrated therein and designated at 10. The electrosurgical illuminating instrument 10 is self-powered by one or more batteries 11 or receives electrical energy from an electrical energy source 20, or is powered by both the batteries 11 and the electrical energy source 20. The proximal end 16 of the electrosurgical illuminating instrument 10 includes a connector 17 that connects the electrosurgical illuminating instrument 10 to the energy source 20 with a lead 18.

The electrosurgical illuminating instrument 10 includes a main body 12, a light pipe 26, a light source 30, and a directing light cover 32. The light source 30 can be any suitable light source, such as, for example, one or more LEDs. If more than one LED is employed, the LEDs can be multicolored. In various arrangements, the light pipe 26 is a bundle of fiber optics.

The electrosurgical illuminating instrument 10 further includes a switch 24 that turns the electrosurgical illuminating instrument 10 on and off. For example, in a particular arrangement the switch includes a first switch 24a that turns the light source 30 on and off and a second switch 24b that activates the energy source 20 to deliver RF electrical energy to a distal end 34 of the electrosurgical illuminating instrument 10. In particular arrangements, the one or more batteries 11 provides electrical energy to the light source 30 and the energy source 20 provides RF electrical energy to the distal end 34 to treat tissue in proximity of the distal end 34.

The electrosurgical illuminating instrument 10 also includes a button 28 that toggles the electrosurgical illuminating instrument 10 from wide illumination of the surgical site to narrow illumination of the site from the distal end 34 of the electrosurgical illuminating instrument 10. More specifically, when the button 28 is in the wide illumination position, the light source 30 is uncovered by the light cover 32 to provide wide illumination of the surgical site as indicated by the arrows 33, and when the button 28 is in the narrow illumination position, the light source 30 rotates downward towards the light cover 32 such that the light cover 32 directs light from the light source 30 to the distal end 34 through the light pipe 26 to provide localized illumination (as indicated by the arrows 36) at the surgical site. Accordingly, a medical professional is able to illuminate and view local tissue to be treated to accurately perform a surgical procedure with the electrosurgical illuminating instrument 10. Further, the electrosurgical illuminating instrument 10 meets the strict waterproofing and sanitizing requirements of a surgery room.

Figure 3:
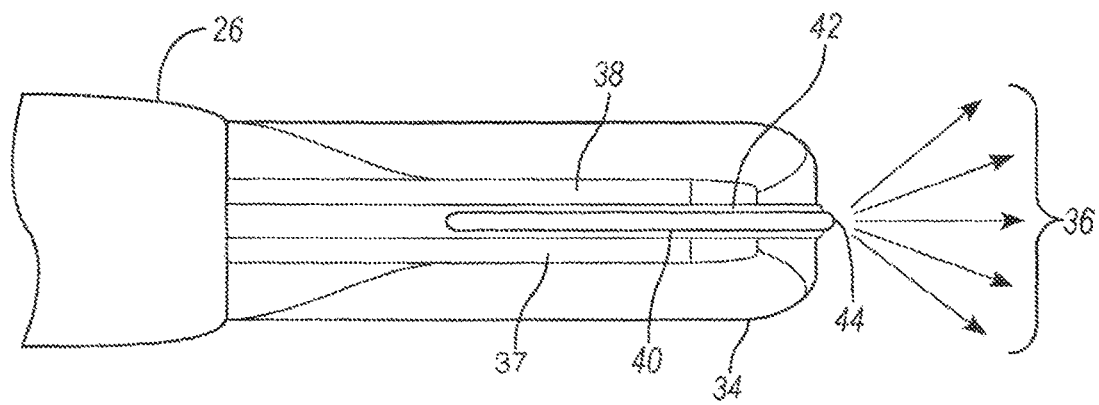
FIG. 3 is a close-up view of a distal end of the electrosurgical illuminating instrument.

Referring now to FIG. 3, the distal end 34 of the electrosurgical illuminating instrument 10 is shown in greater detail. As described above the distal end 34 receives light from the light pipe 26. Hence, the distal end 34 can be a second light pipe that optically communicates with the light pipe 26 or an extension of the light pipe 26. The distal end 34 of the electrosurgical illuminating instrument 10 includes a first conductor 37, a second conductor 38, and an insulation material 40, 42 positioned between the first conductor 37 and 38. In some arrangements, the insulation material 40, 42 can be a single piece of insulation material or in other arrangements the insulation material 40, 42 can include a portion separated by a spacer 44.

In various arrangements, the insulation material 40, 42 is translucent, whereas in other arrangements the insulation material 40, 42 is transparent. In particular arrangements, the insulation material includes a transparent portion and a translucent portion. Some portion or portions of the insulation material 40, 42 may be opaque so that light is not transmitted from the opaque portions. All or a portion of the insulation material 40, 42 may be frosted to diffuse the light.

The insulation material can be made from any suitable material, such as, for example, ceramic, silicone rubber, glass, or titanium dioxide, or any combination of these materials.

The first conductor 37 and the second conductor 38 can operate as bipolar electrodes of the electrosurgical instrument 10. In such arrangements, the first and second conductors receive RF electrical energy from, for example, the energy source 20 such that a voltage potential is generated between the first conductor 36 and the second conductor 38, which causes a current to pass from one conductor to the other through tissue being treated by the electrosurgical illuminating instrument 10. This current heats the tissue to coagulate or cauterize the tissue depending on the amount of RF energy supplied to the conductors 37 and 38.

In some arrangements, a portion of the insulation material 40, 42 acts as an indicator to provide visual feedback to the medical profession about the instrument state of the electrosurgical illuminating instrument 10. For example, the color of the light can change from one color to another color after a particular procedure (such as coagulation or cauterization of tissue) is completed. In particular arrangements, the light source 30 is configured to blink, for example, at different frequencies, to indicate various instrument states of the electrosurgical illuminating instrument 10.

The description of the invention is merely exemplary in nature and variations that do not depart from the gist of the invention are intended to be within the scope of the invention. Such variations are not to be regarded as a departure from the spirit and scope of the invention.

What is claimed is:

1. An electrosurgical instrument comprising:
a handpiece comprising a body portion;
a light pipe extending from a proximal end coupled to the handpiece to a distal end;
a directing light cover coupled to the light pipe;
a source coupled to an external surface of the body portion, wherein the light source is rotatable; and
a button on the body portion configured to rotate the light source,
wherein the light source is configured to emit light from the light source for wide illumination,
wherein the light pipe is configured to transmit light between the proximal end configured to receive light from the light source and the distal end configured to emit light for localized illumination, the light cover positioned adjacent to the light source; and
an insulation material disposed between a first conductor and a second conductor and configured to transmit light from an incident surface in optical communication with the distal end of the light pipe to an emitting surface configured to emit light.

2. The electrosurgical instrument of claim 1 wherein the insulation material is translucent.

3. The electrosurgical instrument of claim 1, wherein the insulation material is configured to illuminate a surgical site with light transmitted via the light pipe from the light source.

4. The electrosurgical instrument of claim 1, wherein the emitting surface is located at distal ends of the first and second conductors, lateral sides of the first and second conductors, or both the distal ends and the lateral sides of the first and second conductors.

5. The electrosurgical instrument of claim 1, wherein the insulation material is configured to display an instrument state of the electrosurgical instrument.

6. The electrosurgical instrument of claim 5, wherein the emitting surface comprises a diffuser surface to diffuse light.

7. An electrosurgical instrument comprising:
a handpiece including a body portion;
a light pipe extending from a proximal end to a distal end, the light pipe configured to transmit light;
a directing light cover coupled to the light pipe;
a light source coupled to an external surface of the body portion, wherein the light source is rotatable;
a button on the body portion configured to rotate the light source; and
a surgical end coupled to the distal end of the light pipe, the surgical end including:
an insulation material comprising:
an incident surface configured to receive light from the light source;
an emitting surface configured to emit light and positioned relative to a location selected from a group consisting of:
distal ends of a first conductor and a second conductor; and
lateral sides of the first conductor and the second conductor.

8. The electrosurgical instrument of claim 7 wherein the emitting surface is located at the distal ends of the first and second conductors.

9. The electrosurgical instrument of claim 7 wherein the emitting surface is configured to display an instrument state of the electrosurgical instrument and the emitting surface comprises a diffuser surface.

10. A surgical instrument comprising:
a handpiece comprising a body portion;
a surgical end;
a light pipe extending from a proximal end adjacent to the handpiece to a distal end adjacent to the surgical end, the light pipe configured to transmit light from the light source
a directing light cover coupled to the light pipe;
a light source coupled to an external surface of the body portion, wherein the light source is rotatable; and
a button on the body portion configured to rotate the light source.

11. The surgical instrument of claim 10 wherein the surgical end comprises an insulation material disposed between a first conductor and a second conductor, the insulation material comprising:
an incident surface configured to receive light from a light source; and
an emitting surface configured to emit light for localized illumination of the surgical site and positioned relative to a location selected from a group consisting of:
distal ends of the first conductor and the second conductor, and
lateral sides of the first conductor and the second conductor.

12. The surgical instrument of claim 10 further comprising an insulation material disposed between a first conductor and a second conductor and configured to transmit light from an incident surface in optical communication with the distal end of the light pipe to an emitting surface configured to emit light.

13. The surgical instrument of claim 10 further comprising an insulation material disposed between a first electrode and a second electrode and configured to transmit light from an incident surface in optical communication with the distal end of the light pipe to an emitting surface configured to emit light,
wherein the insulation material is configured to display an instrument state of the surgical instrument.

14. The surgical instrument of claim 13 wherein the emitting surface comprises a diffuser surface to diffuse light.

* * * * *

UNITED STATES PATENT AND TRADEMARK OFFICE
CERTIFICATE OF CORRECTION

PATENT NO. : 11,135,032 B2
APPLICATION NO. : 16/090954
DATED : October 5, 2021
INVENTOR(S) : Blus et al.

Page 1 of 1

It is certified that error appears in the above-identified patent and that said Letters Patent is hereby corrected as shown below:

In the Claims

In Column 5, Line 17, in Claim 1, after "a", insert --light--

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*